United States Patent [19]

Bacich

[11] Patent Number: 5,472,419
[45] Date of Patent: Dec. 5, 1995

[54] CATHETER AND METHOD FOR DEPOSITING REPRODUCTIVE MATERIAL INTO THE REPRODUCTIVE TRACT OF A FEMALE

[75] Inventor: Steven R. Bacich, Laguna Niguel, Calif.

[73] Assignee: Imagyn Medical, Inc., Laguna Niguel, Calif.

[21] Appl. No.: 189,050

[22] Filed: Jan. 31, 1994

[51] Int. Cl.⁶ .................... A61M 31/00; A61M 25/00; A61B 17/43; A61B 17/42
[52] U.S. Cl. ............... 604/55; 604/280; 604/906; 600/35; 606/119
[58] Field of Search .................. 604/43, 164, 280, 604/55, 73, 218, 906, 171; 600/35; 606/119

[56] References Cited

U.S. PATENT DOCUMENTS

| | | |
|---|---|---|
| 1,586,716 | 6/1926 | Snow, Jr. . |
| 2,024,982 | 12/1935 | Scott . |
| 3,481,338 | 12/1969 | Sobel et al. . |
| 3,605,750 | 9/1971 | Sheridan et al. . |
| 3,774,612 | 11/1973 | Marco . |
| 4,013,079 | 3/1977 | Lindemann et al. . |
| 4,136,695 | 1/1979 | Dafoe . |
| 4,211,233 | 7/1980 | Lin . |
| 4,243,040 | 1/1981 | Beecher . |
| 4,271,839 | 6/1981 | Fogarty et al. . |
| 4,321,915 | 3/1982 | Leighton et al. . |
| 4,437,857 | 3/1984 | Goldstein et al. . |
| 4,530,698 | 7/1985 | Goldstein et al. . |
| 4,604,094 | 8/1986 | Shook . |
| 4,642,094 | 2/1987 | North, Jr. et al. . |
| 4,774,949 | 10/1988 | Fogarty . |
| 4,790,814 | 12/1988 | Fischl et al. . |
| 4,863,423 | 9/1989 | Wallace . |
| 4,865,589 | 9/1989 | Simmet et al. . |
| 4,990,138 | 2/1991 | Bacich et al. . |

(List continued on next page.)

FOREIGN PATENT DOCUMENTS 542519  1/1977  U.S.S.R. .

OTHER PUBLICATIONS

"IVF Products", Cook IVF, Cook Australia brochure, pp. 22, 24–32, 42, 43, 46.

"Transcervical access and intra–luminal imaging of the Fallopian tube in the non–anaesthetized patient; Preliminary results using a new technique for Fallopian access", Otmar Bauer et al, Human Reproduction, vol. 7 suppl. 1, pp. 7–11, 1992.

"The linear everting catheter: a nonhysteroscopic, trans–vaginal technique for access and microendoscopy of the fallopian tube", Pearlstone et al, Fertility and Sterility, vol. 68 No. 4, Oct. 1992.

"Nonoperative Embryo Transfer to the Fallopian Tube", Jansen et al, The New England Journal of Medicine, pp. 288–290, Aug. 4, 1988.

"Retrograde tubal transfer of human embryos", Risquez et al, Human Reproduction, pp. 185–188, 1990.

"Gemete intrafallopian transfer by hysteroscopy as an alternative treatment for infertility", Possati et al, Fertility and Sterility, vol. 56, No. 3, Sep. 1991, pp. 496–499.

"Transcervical Intra Fallopian Endoscopy–Falloposcopy", Focus on Reproduction, Jan. 1993, Bauer et al.

Primary Examiner—C. Fred Rosenbaum
Assistant Examiner—Perry E. Van Over
Attorney, Agent, or Firm—Gordon L. Peterson; Donald E. Stout

[57] ABSTRACT

A method of depositing reproductive material into the reproductive tract of a female comprising inserting an elongated transfer catheter into the reproductive tract of a female. The transfer catheter includes an elongated catheter body having an elongated passage extending through the catheter body and terminating in a distal opening at a distal end of the catheter body. The distal opening opens both axially and laterally of the catheter body. The method also includes introducing the reproductive biological material through the passage and the distal opening of the catheter body into the reproductive tract.

19 Claims, 3 Drawing Sheets

U.S. PATENT DOCUMENTS

| | | |
|---|---|---|
| 5,108,366 | 4/1992 | Schatz . |
| 5,147,315 | 9/1992 | Weber . |
| 5,163,927 | 11/1992 | Worker et al. . |
| 5,171,305 | 12/1992 | Schickling et al. . |
| 5,195,979 | 3/1993 | Schinkel et al. . |
| 5,226,426 | 7/1993 | Yoon . |
| 5,236,423 | 8/1993 | Mix et al. . |
| 5,259,364 | 11/1993 | Bob et al. . |
| 5,273,527 | 12/1993 | Schatz et al. . |
| 5,290,282 | 3/1994 | Casscells . |
| 5,374,247 | 12/1994 | Lowery et al. . |

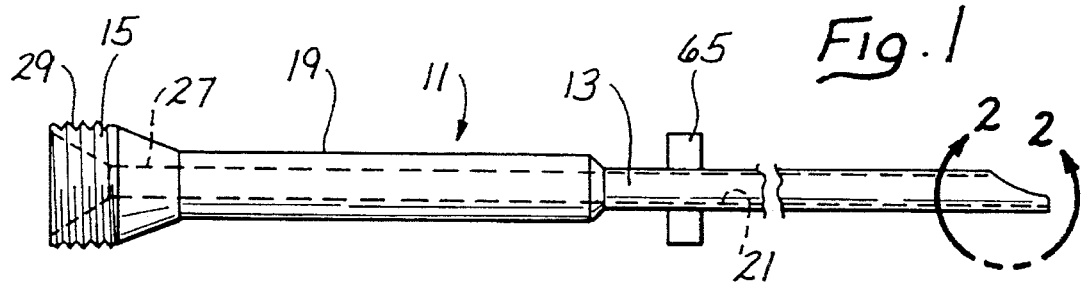
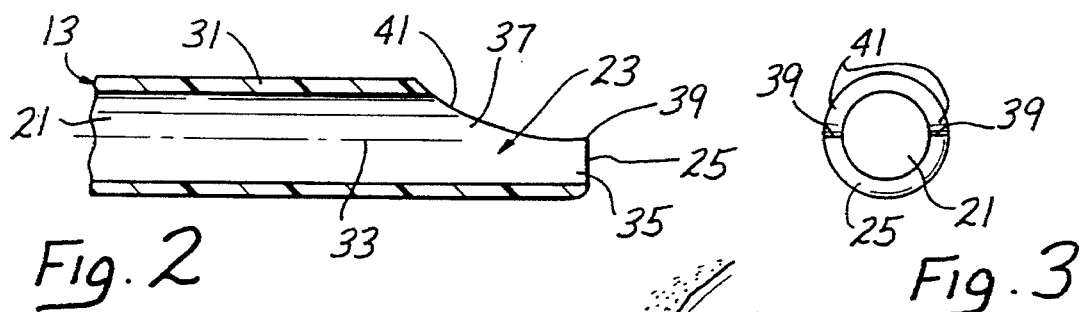
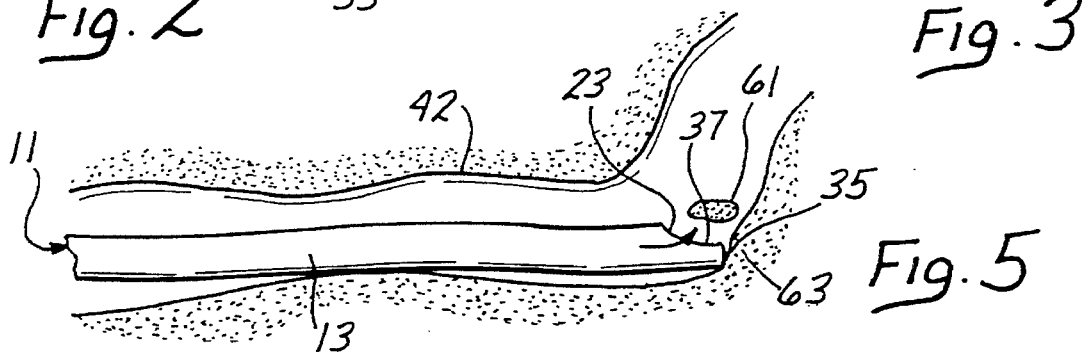
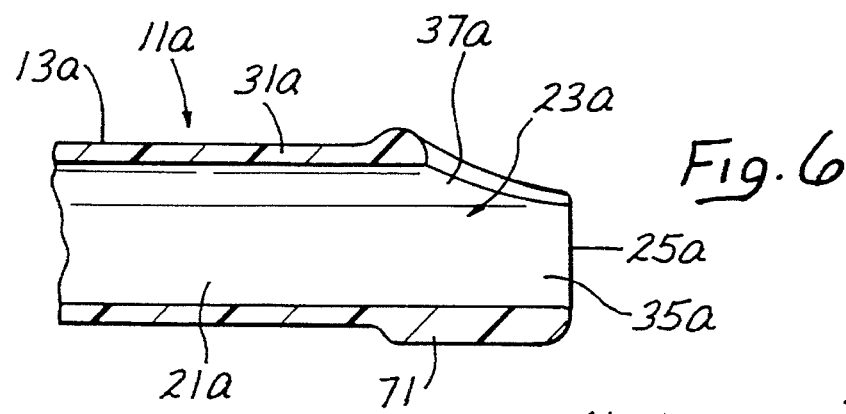
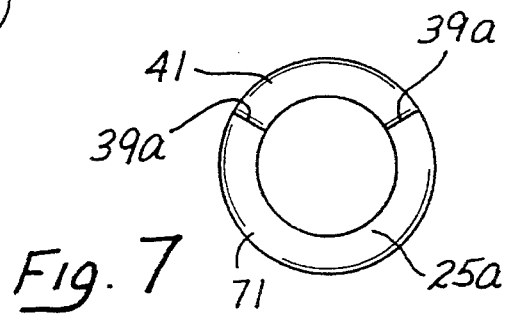

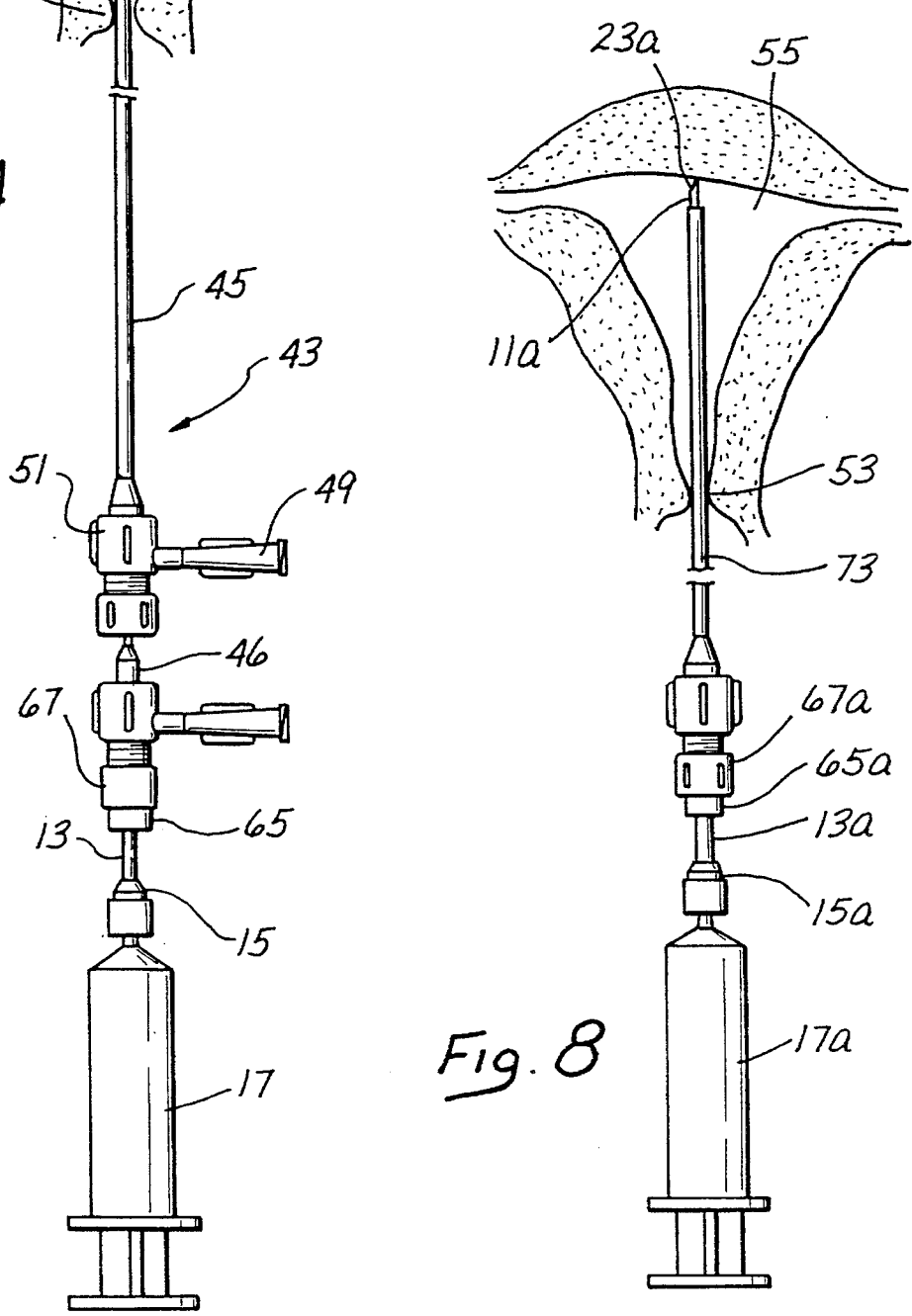

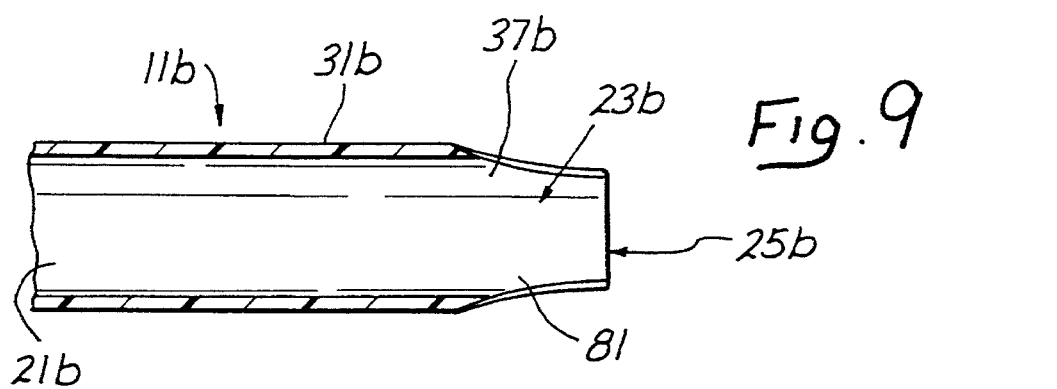
Fig. 9
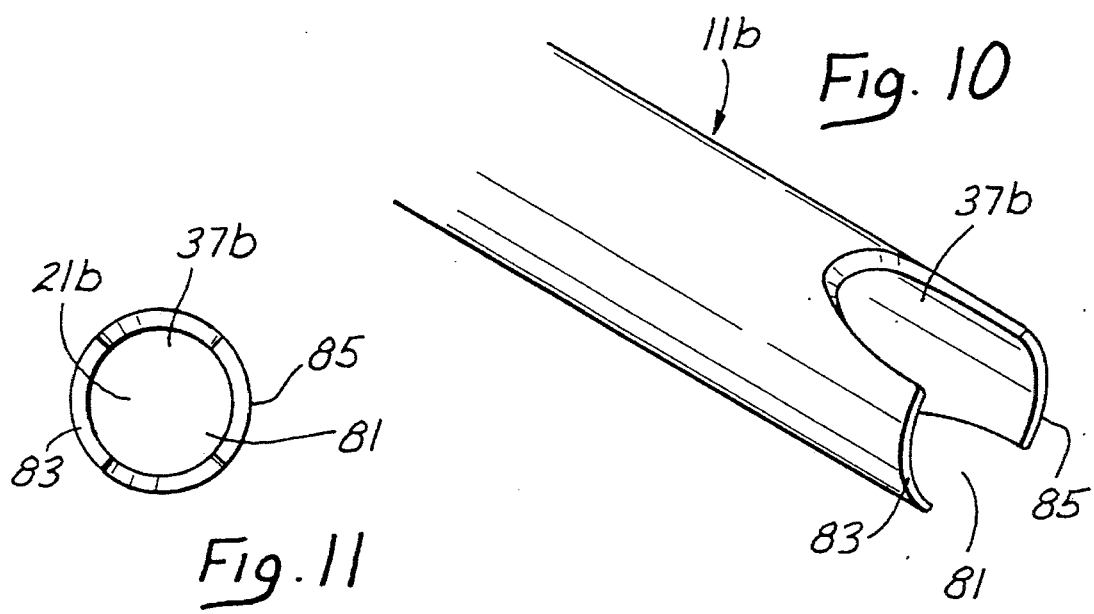
Fig. 10
Fig. 11
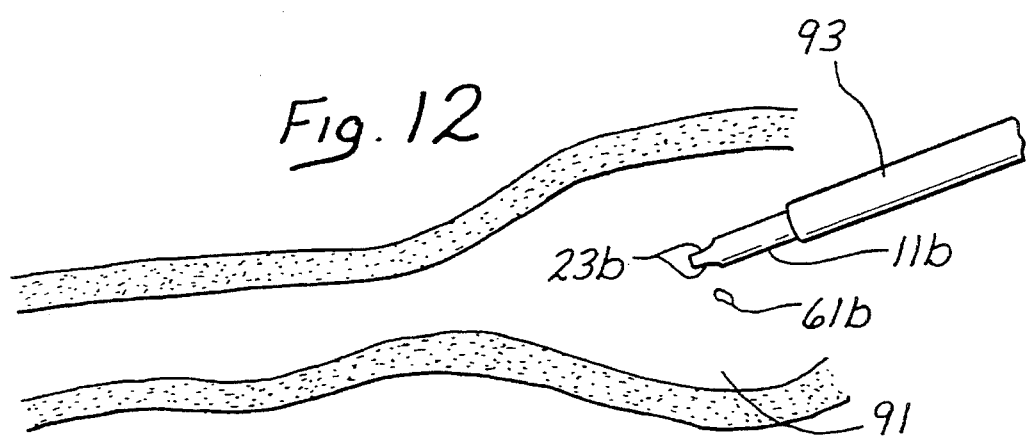
Fig. 12

CATHETER AND METHOD FOR DEPOSITING REPRODUCTIVE MATERIAL INTO THE REPRODUCTIVE TRACT OF A FEMALE

BACKGROUND OF THE INVENTION

This invention relates generally to the field of infertility medicine and more specifically to a method and transfer catheter for use in assisted reproduction.

In assisted reproduction, reproductive material is introduced into a reproductive tract of a female. For example, the reproductive material may be embryos, gametes and zygotes. The reproductive material may be introduced transcervically to the uterus or fallopian tube using an appropriate transfer catheter and/or catheter system or introduced into the fallopian tube using laparoscopic techniques.

The insertion technique and/or the anatomy into which the transfer catheter is to be inserted impose size limitations on the catheter. This is particularly true for gamete intra-fallopian tube transfer (GIFT) procedures performed in a transvaginal route in which the internal diameter of the proximal portions of the fallopian tube (intramural and isthmic) can be as small as 0.75 millimeter. This imposes a significant constraint on the external cross sectional dimensions of the transfer catheter. In addition, the internal diameter of the transfer catheter should not be smaller than about 0.4 millimeter because forcing an embryo into a smaller lumen may be harmful to the embryo or detrimental to the process of loading or expelling the embryo from the transfer catheter.

With these small diameters, a transfer catheter can easily have its distal opening occluded when the catheter contacts soft tissues. When this occurs, a relatively high pressure is required to expel the reproductive material from the transfer catheter and this can result in a failed transfer or damage to the cells as a result of the high pressure applied to them through the transfer catheter.

One type of prior art transfer catheter has a distal opening lying in a plane which is perpendicular to the central axis of the catheter. This axially opening distal opening can be rather easily occluded.

Another type of prior art transfer catheter has a side opening rather than an axial opening. However, the side opening is also subject to occlusion when it comes into contact with tissue and this can happen, for example, because of the tortuous path defined by the fallopian tube. In addition, this type of transfer catheter is relatively difficult to manufacture and a large side opening proximal of the distal end would weaken the catheter and create a propensity to kink. Although other port arrangements are known for catheters used in other regions of the body, such as the vasculature, so far as I am aware none of them is adapted for the deposition of reproductive material into the reproductive tract of a female.

SUMMARY OF THE INVENTION

This invention provides a method and transfer catheter for depositing reproductive material into the reproductive tract of a female which generally overcomes the disadvantages noted above. With this invention, the likelihood of occlusion of the distal opening of the transfer catheter is significantly reduced. Consequently, the likelihood of successfully accomplishing the deposition of the reproductive material into the reproductive tract is enhanced.

This invention employs a transfer catheter which includes an elongated catheter body having an elongated passage extending through the catheter body and terminating in a distal opening at a distal end of the catheter body. The distal opening opens both axially and laterally of the catheter body. Consequently, the reproductive material can exit the transfer catheter through the lateral portion of the distal opening even if the axial portion is pushed against tissue. In addition, the provision of a distal opening which opens both axially and laterally produces a reduced profile (as viewed in side elevation) of the distal portion of the transfer catheter thereby reducing the resistance to insertion and forward movement of the catheter in the patient.

In the method of this invention, this transfer catheter is inserted into the reproductive tract of a female and reproductive biological material is introduced through the passage of the transfer catheter and the distal opening of the catheter body into the reproductive tract. The insertion may be accomplished transcervically through the uterus into a fallopian tube or transcervically into the uterus. In the former case, the reproductive material is introduced into the fallopian tube and in the latter case into the uterus. Also, the transfer catheter may be inserted into the fallopian tube using laparoscopic techniques with a subsequent introduction of the reproductive material into the fallopian tube.

To reduce the likelihood of trauma, the distal end of the transfer catheter is preferably substantially blunt. Although bluntness can be brought about in different ways, preferably the distal end extends through an arc of at least 120°. Also, it is preferred that the distal end lie substantially in a radial plane, i.e. a plane which is substantially perpendicular to the longitudinal axis of the catheter body. If the arc of the distal end is less than 120°, there is some additional risk of tissue damage. On the other hand, a distal end arc that is greater than 240° tends to reduce the benefit of the laterally opening portion of the distal opening and this is particularly true for transfer catheters adapted for transcervical entry into the fallopian tube.

Certain dimensional parameters are also important and vary depending upon the manner in which the transfer catheter is to be used. For example, GIFT transfer catheters preferably have a maximum cross sectional dimension in a distal region of no more than about 3.5 millimeters with no more than about 0.7 millimeter being preferred and a maximum cross sectional dimension of the passage in such distal region of no more than about 2 millimeters with no more than about 0.5 millimeter being preferred. Although these dimensions preferably extend throughout a major length of the transfer catheter, they should at least be applicable in a distal region of the catheter body which extends to the distal end and which is between about 0.5 millimeter and about 4 millimeters in length.

For GIFT transfer catheters, the length of the laterally opening portion of the distal opening should not be less than about 0.5 millimeter and not greater than about 4 millimeters. Lengths less than about 0.5 millimeter may reduce the size of the laterally opening portion of the distal opening too much whereas lengths greater than about 4 millimeters tend to create a laterally opening portion which is so large as to increase the difficulty in loading the transfer catheter with the reproductive biological material.

For transfer catheters used for the transfer of fertilized embryos to the uterus (IVF), the maximum cross sectional dimension of the distal region may be no more than about 3.5 millimeters with no more than about 1.5 millimeters being preferred and the maximum cross sectional dimension of the passage may be no more than about 3 millimeters with no more than about 1 millimeter being preferred. These size increases are acceptable because the dimensional constraints imposed by the fallopian tube are not applicable to this form of the transfer catheter. In addition, the distal end can extend through an arc greater than 240° and still provide a laterally opening portion of the distal opening of a suitable size for embryos. However, the axial dimension of the laterally opening portion is preferably no more than about 3 millimeters in order to prevent the loading procedure from becoming too difficult. Another feature of this IVF transfer catheter is that it may include a circumferentially extending enlargement around the distal opening which is provided for minimizing trauma. For example, this circumferentially extending enlargement may radially thicken the wall of the transfer catheter by no more than about 0.2 millimeter and preferably thickens the wall by about 0.1 millimeter to about 0.15 millimeter. This enlargement may have a maximum axial length which is slightly more than the axial dimension of the laterally opening portion of the distal opening.

The distal opening of the transfer catheter may include, in addition to the axially opening portion, first and second laterally opening portions. In this event, the distal end includes first and second distal end segments which are separated circumferentially by the first and second laterally opening portions. A transfer catheter of this type is considered preferable for transcervical insertion into the uterus or insertion into the distal region of the fallopian tube using laparoscopic techniques. The maximum cross sectional dimension of the distal region of this transfer catheter is no more than about 3.5 millimeters with up to about 1.25 millimeters being preferred and the maximum cross sectional dimension of the passage in such distal region is no more than about 2.5 millimeters with up to about 1 millimeter being preferred.

The invention, together with additional features and advantages thereof may best be understood by reference to the following description taken in connection with the accompanying illustrative drawings.

BRIEF DESCRIPTION OF THE DRAWINGS

FIG. 1 is a side elevational view of a transfer catheter constructed in accordance with the teachings of this invention.

FIG. 2 is an enlarged, fragmentary, axial sectional view through a distal portion of the catheter.

FIG. 3 is an end elevational view of the catheter.

FIG. 4 is a schematic view illustrating the use of the transfer catheter to introduce reproductive biological material into a fallopian tube.

FIG. 5 is an enlarged fragmentary sectional view illustrating the introduction of the reproductive biological material into a fallopian tube which defines a tortuous path.

FIG. 6 is an enlarged fragmentary, axial sectional view similar to FIG. 2 illustrating a second form of transfer catheter which is adapted for the introduction of reproductive biological material into the uterus.

FIG. 7 is an end elevational view of the transfer catheter of FIG. 6.

FIG. 8 is a view illustrating the use of the transfer catheter of FIGS. 6 and 7 to introduce reproductive biological material into the uterus.

FIG. 9 is an enlarged, fragmentary, axial sectional view similar to FIG. 3 illustrating a third form of transfer catheter.

FIG. 10 is a perspective view of the distal portion of the transfer catheter of FIG. 9.

FIG. 11 is an end elevational view of the transfer catheter of FIG. 9.

FIG. 12 is a view illustrating the use of laparoscopic techniques for insertion of the catheter into the fallopian tube and the introduction of the reproductive biological material into the fallopian tube.

DESCRIPTION OF THE PREFERRED EMBODIMENT

FIG. 1 shows a transfer catheter 11 which generally includes an elongated, flexible catheter body 13, a proximal adapter 15 for coupling the catheter to a syringe 17 (FIG. 4), and a strain relief tube 19. The catheter body 13 may be constructed of polytetrafluoroethylene or other biocompatible, flexible material which is inert with respect to the reproductive biological material with which it is to be used. The catheter body 13 is preferably cylindrical. The catheter body 13 has an elongated cylindrical passage 21 which extends axially completely through the catheter body and terminates in a distal opening 23 at a distal end 25 of the catheter body.

The adapter 15, which may be constructed for example of stainless steel, polytetrafluoroethylene, polyethylene or other biocompatible polymer is suitably fixed to a proximal region 27 of the catheter body 13 as by bonding and has Luer threads 29 or other suitable connector features to enable it to be releasably coupled to the syringe 17 (FIG. 4).

The strain relief tube 19 may be bonded to the catheter body and to the adapter 15. The strain relief tube 19 may be constructed for example of polyimide, polytetrafluoroethylene or other biocompatible polymeric material. The adapter 15 and the strain relief tube 19 may be conventional.

A distal region 31 of the catheter body 13 is of particular interest. The distal region 31 extends from the distal end 25 for a distance of at least 0.5 millimeter and no more than about 4 millimeters.

The transfer catheter 11 is particularly adapted for introducing reproductive biological material into the fallopian tube. As such, the distal region 31 has a maximum cross sectional dimension (diameter in the example shown in FIGS. 1–3) of no more than about 0.7 millimeter although larger diameters up to 3.5 millimeters can be employed. In addition, the maximum cross sectional dimension (diameter in the example shown in FIGS. 1–3) of the passage 21 in the distal region 31 is no more than about 0.5 millimeter although larger diameters up to 2 millimeters can be employed. In this embodiment, these dimensions prevail throughout the full length of the catheter body 13.

The distal end 25 is blunt, and in this embodiment lies in a radial plane, i.e. lies in a plane which is perpendicular to a longitudinal or central axis 33. Although the distal end may sweep an arc of from about 120° to about 240°, in this embodiment it sweeps an arc of about 180° and this arc length is preferred. This arc length coupled with the radial orientation of the distal end 25 provide the desired bluntness for the distal end.

The distal opening 23 has an axially opening portion 35 and a laterally opening portion 37 which are interconnected such that the distal opening 23 provides a single relatively large opening. Although the full cross sectional area of the passage 21 opens in the axial direction, it is convenient to define the axially opening portion 35 as that axially opening region of the passage 21 which is coextensive with the distal end 25. The laterally opening portion 37 may be considered as that portion of the opening which extends from the opposite edges 39 (FIG. 3) of the distal end 35 proximally.

The laterally opening portion 37 has side edges 41 which are concavely curved as viewed in side elevation (FIG. 2). Although the concave curve is preferred in order to increase the area of the laterally opening portion 37, it is not essential. The laterally opening portion 37 extends from the distal end 25 proximally for at least about 0.5 millimeter and no more than about 4 millimeters, and in the embodiment illustrated extends proximally for about 1 millimeter.

Although the transfer catheter 11 may be used in different ways, it is particularly adapted for introducing reproductive biological material into a fallopian tube 42 (FIG. 4) via a transcervical route. This is illustrated in FIGS. 4 and 5. In FIG. 4 the transfer catheter 11 is being used with a conventional everting catheter 43 such as the everting catheter disclosed in Woker et al U.S. Pat. No. 5,163,927 which is incorporated by reference herein. Although various techniques can be used to deliver the transfer catheter 11 to the fallopian tube 42, the everting catheter 43 is preferred.

The linear everting catheter 43 includes an outer tube 45, an inner tube 46 movable axially in the outer tube and a flexible everting element 47 coupled to the distal end portions of the outer and inner tubes. By applying a fluid under pressure through a leg 49 of a fitting 51 which is coupled to the outer tube 45 and moving the inner tube 46 distally, the everting element 47 can be everted out of the outer tube 45 in a conventional and well known manner.

The everting catheter 43 can be used in different ways to place the transfer catheter 11 into the fallopian tube 42. For example, the everting catheter 43 with the transfer catheter 11 within it can be inserted through the cervix 53 and the uterus 55 (FIG. 4) to position the distal end 57 of the outer tube 45 substantially at the ostium 59 of the fallopian tube 42. The everting element 47 is then everted into the fallopian tube 42 and this carries the transfer catheter 11 with it.

The adapter 15 is coupled to a syringe 17 in any suitable manner such as by the Luer threads 29 (FIG. 1) and complementary threads (not shown) on the syringe. The syringe 17 is loaded with the reproductive biological matter, such as gametes, in liquid form. When the desired location within the fallopian tube 42 has been reached, the syringe 17 is operated to apply sufficient fluid pressure to the reproductive biological material within it to transfer it through the passage 21 and the distal opening 23 into the fallopian tube 42. As shown somewhat schematically in FIG. 5, the reproductive biological material 61 can be passed through the distal opening 23 even if tissue 63 tends to block a portion of the axially opening portion 35. The transfer catheter 11 can be delivered to the fallopian tube 42 in other ways and the technique described above is purely illustrative.

A number of techniques can be used to ascertain when the desired location within the fallopian tube 42 has been reached. For example, a positioning marker 65 can be used to mark the location on the catheter body 13 to indicate that the distal end 25 extends the desired distance beyond the everting catheter 43. The positioning marker 65, which may be constructed of silicone, may form a slidable friction fit on the catheter body 13. Prior to insertion of the everting catheter 43 into the reproductive tract, the transfer catheter 11 may be inserted into the everting catheter 43 and the everting catheter everted until the distal end 25 extends the desired distance beyond the end of the everting catheter. The positioning marker 65 can then be slid into engagement with the proximal end of the fitting 67 on the inner tube 46 of the everting catheter 43 to mark this position. In actual use of the transfer catheter 11 and the everting catheter 43, the eversion of the everting catheter is carried out until the positioning marker 65 contacts the fitting 67 as shown in FIG. 4 to thereby indicate that the distal end 25 now protrudes sufficiently from the everting catheter.

FIGS. 6 and 7 show a transfer catheter 11a which is identical to the transfer catheter 11 in all respects not shown or described herein. Portions of the transfer catheter 11a corresponding to portions of the transfer catheter 11 are designated by corresponding reference numerals followed by the letter a. The transfer catheter 11a is particularly adapted for IVF use to place reproductive biological material into the uterus 55 as shown by way of example in FIG. 8. As such, the catheter 11a has a circumferentially extending enlargement 71 around the distal opening 23a. In this embodiment, the enlargement 71 extends completely and continuously around the catheter body 13a for a full 360°. The enlargement 71 extends longitudinally for a length greater than the extent to which the laterally opening portion 37a extends proximally of the distal end 25a. In the embodiment illustrated, the length of the enlargement 71 axially along the bottom (as viewed in FIG. 6) is about 1 millimeter and the enlargement extends radially beyond the outer diameter of the catheter body 13a immediately adjacent the enlargement by about 0.1 millimeter.

The distal end 25a in the embodiment illustrated extends through an arc about 240°. The diameter of the catheter body 13a at the enlargement 71 preferably does not exceed about 1.5 millimeters and the internal diameter of the passage 21a is no more than about 1 millimeter although larger diameters for the enlargement and passage can be used, if desired. The wall thickness of the catheter body 13a away from the enlargement 71 in this embodiment is about 0.15 millimeter. The laterally opening portion 37a extends proximally from the distal end 25a at least about 0.5 millimeter and no more than about 3 millimeters, and in this embodiment, it extends proximally from the distal end about 1 millimeter.

The catheter body 13a can be inserted into the uterus 55 in various different ways. As shown in FIG. 8, a relatively rigid guiding catheter 73 is inserted through the cervix 53 into the uterus 55. The transfer catheter 11a is then inserted through the guiding catheter 73 to place the distal opening 23 at the desired location within the uterus 55. Alternatively, the transfer catheter 11a may be inserted through the cervix 53 with the guiding catheter 73. When in position as determined by the positioning marker 65a, the syringe 17a is manually operated to apply sufficient fluid pressure to the reproductive biological material to introduce it through the passage 21a and the distal opening 23a to the uterus 55. In this instance, the reproductive biological material is fertilized embryos.

FIGS. 9–12 show a transfer catheter 11b which is identical to the transfer catheter 11 in all respects not shown or described herein. Portions of the transfer catheter 11b corresponding to portions of the transfer catheter 11 are designated by corresponding reference numerals followed by the letter b.

One difference between the catheters 11b and 11 is that the distal opening 23 of the former has a first laterally opening portion 37b and a second laterally opening portion 81. The distal end 25b includes distal end segments 83 and 85 (FIGS. 10 and 11), and the distal end segments are separated circumferentially by the laterally opening portions 37b and 81. In this embodiment, the laterally opening portions 37b and 81 are diametrically opposed, are of equal size and of the same shape. Each of the laterally opening portions 37b and 81 extends proximally from the distal end 25b for at least about 0.5 millimeter and no more than about 4 millimeters. In this embodiment., the laterally extending openings 37b and 81 extend proximally from the distal end 25b about 1 millimeter. Each of the distal end segments 83 and 85 extend circumferentially through an arc of at least about 90° and not more than 120°. In the embodiment illustrated, each of the distal end segments 83 and 85 extends through an arc of about 90°. Although larger diameters may be employed, in this embodiment the outside diameter of the distal region 31 is no more than about 1.25 millimeters and the diameter of the passage 21b is no more than about 1 millimeter.

The transfer catheter 11b is particularly adapted for introducing reproductive biological material into the uterus as shown by way of example in FIG. 8 or for introducing reproductive biological material into a distal region 91 of the fallopian tube 42 as shown in FIG. 12. In FIG. 12, a working channel to the distal region 91 is established laparoscopically using a trocar cannula 93 and conventional laparoscopic techniques. The transfer catheter 11b is then inserted through the working channel of the trocar cannula 93 into the distal region 91 of the fallopian tube. Reproductive biological material such as embryos is then forced through the passage 21b and the distal opening 23b and out the distal opening 23 into the distal region 91 of the fallopian tube. The pressure for forcing the reproductive biological material into the fallopian tube can be provided by a syringe, such as the syringe 17 (not shown in FIG. 12).

Although exemplary embodiments of the invention have been shown and described, many changes, modifications and substitutions may be made by one having ordinary skill in the art without necessarily departing from the spirit and scope of this invention.

I claim:

1. A method of depositing reproductive biological material into the reproductive tract of a female comprising:

inserting an elongated transfer catheter into the reproductive tract of a female wherein the transfer catheter includes an elongated catheter body having an elongated passage extending through the catheter body and terminating in a distal opening at a distal end of the catheter body, and said distal opening opens both axially and laterally of the catheter body; and introducing the reproductive biological material through the passage and the distal opening of the catheter body into the reproductive tract.

2. A method as defined in claim 1 wherein the step of inserting includes inserting the catheter transcervically through the uterus into a fallopian tube and the step of introducing includes introducing the reproductive biological material through the passage and the distal opening into the fallopian tube.

3. A method as defined in claim 1 wherein the step of inserting includes inserting the catheter transcervically into the uterus and the step of introducing includes introducing the reproductive biological material through the passage and the distal opening into the uterus.

4. A method as defined in claim 1 wherein the step of inserting includes laparoscopically establishing a working channel to a region of a fallopian tube, inserting the catheter through the working channel into the fallopian tube and the step of introducing includes introducing the reproductive biological material through the passage and the distal opening into the fallopian tube.

5. A method as defined in claim 1 wherein the distal end of the transfer catheter is substantially blunt and the laterally opening portion of the distal opening extends proximally of the distal end for no more than about 4 millimeters.

6. A method of depositing reproductive biological material into the reproductive tract of a female comprising:

providing a catheter which includes an elongated catheter body having a distal end and an elongated passage terminating in a distal opening at the distal end, the distal opening having an axially opening portion and a laterally opening portion, said laterally opening portion extending from the distal end proximally for at least about 0.5 millimeter and no more than about 4 millimeters, said distal end extending circumferentially for at least about 120 degrees, said distal end being substantially blunt, said catheter body having a distal region which extends to the distal end and which is between about 0.5 millimeter and about 4 millimeters in length, the distal region having a maximum cross sectional dimension of no more than about 3.5 millimeters and said passage having a maximum cross sectional dimension of no more than about 3.0 millimeters;

inserting the catheter body into the reproductive tract of a female to place the distal region and the distal opening within the reproductive tract; and introducing the reproductive biological material through the passage and the distal opening of the catheter body into the reproductive tract.

7. A catheter for introducing reproductive material into the female reproductive tract comprising:

an elongated catheter body having a distal end and an elongated passage terminating in a distal opening at the distal end;

said distal opening having an axially opening portion and a laterally opening portion, said laterally opening portion extending from the distal end proximally for at least about 0.5 millimeter and no more than about 4 millimeters, said distal end extending circumferentially for at least about 120 degrees, said laterally opening portion having side edges; and said distal end lying substantially in a radial plane.

8. A catheter as defined in claim 7 wherein the distal end extends circumferentially for no more than about 240 degrees.

9. A catheter as defined in claim 7 wherein said catheter body has a distal region which extends to the distal end and which is between about 0.5 millimeter and about 4 millimeters in length and the maximum cross sectional dimension of the distal region is no more than about 1.25 millimeters.

10. A catheter as defined in claim 7 wherein said catheter body has a distal region which extends to the distal end and which is between about 0.5 millimeter and about 4 millimeters in length and the maximum cross sectional dimension of the distal region is no more than about 0.7 millimeter.

11. A catheter as defined in claim 7 wherein said catheter body has a distal region which extends to the distal end and which is between about 0.5 millimeter and about 4 millimeters in length and the maximum cross sectional dimension of the passage in the distal region is no more than about 0.5 millimeter.

12. A catheter as defined in claim 7 wherein the distal end extends circumferentially for at least about 180 degrees and the side edges are concavely curved.

13. A catheter as defined in claim 7 wherein the catheter has a circumferentially extending enlargement around the distal opening.

14. A catheter as defined in claim 13 wherein the enlargement is no more than about 1 millimeter in length.

15. A catheter as defined in claim 7 wherein said laterally opening portion is a first laterally opening portion and said distal opening has a second laterally opening portion, the second laterally opening portion extends from the distal end proximally for at least about 0.5 millimeter and no more than about 4 millimeters, said distal end including first and second distal end segments which are separated circumferentially by said first and second laterally opening portions.

16. A catheter as defined in claim 7 wherein said catheter body has a distal region Which extends to the distal end and which is between about 0.5 millimeter and about 4 millimeters in length, said distal region has a maximum cross sectional dimension of no more than about 1.5 millimeters and said passage in said distal region has a maximum cross sectional dimension of no more than about 1 millimeter.

17. A catheter for introducing reproductive material into the female reproductive tract comprising:

an elongated catheter body having a distal end and an elongated passage terminating in a distal opening at the distal end;

said distal opening having an axially opening portion and a laterally opening portion, said laterally opening portion extending from the distal end proximally for at least about 0.5 millimeter and no more than about 4 millimeters, said distal end extending circumferentially for at least about 120 degrees, said laterally opening portion having side edges;

said catheter body having a distal region which extends to the distal end and which is between about 0.5 millimeter and about 4 millimeters in length;

said distal region having a maximum cross sectional dimension of no more than about 3.5 millimeters and said passage in the distal region having a maximum cross sectional dimension of no more than about 3 millimeters; and a circumferentially extending enlargement around the distal opening.

18. A catheter for introducing reproductive material into the female reproductive tract comprising:

an elongated catheter body having a distal end and an elongated passage terminating in a distal opening at the distal end;

said distal opening having an axially opening portion and first and second laterally opening portions, each of said first and second laterally opening portions extending from the distal end proximally for at least about 0.5 millimeter and no more than about 4 millimeters, said distal end extending circumferentially for at least about 120 degrees, each of said first and second laterally opening portions having side edges; and said distal end including first and second distal end segments which are separated circumferentially by said first and second laterally opening portions.

19. A catheter as defined in claim 18 wherein said catheter body having a distal region which extends to the distal end and which is between about 0.5 millimeter and about 4 millimeters in length, said distal region has a maximum cross sectional dimension of no more than about 3.5 millimeters and said passage in said distal region has a maximum cross sectional dimension of no more than about 2.5 millimeters, said distal end including first and second distal end segments which are separated circumferentially by said first and second laterally opening portions.

* * * * *